United States Patent

Kuboki

[11] 4,184,251
[45] Jan. 22, 1980

[54] INSTRUMENT FOR PROCESSING ARTIFICIAL TEETH AND THE LIKE

[76] Inventor: Tamotsu Kuboki, 1-14-27, Nishifuna, Funabashi-shi, Chiba-ken, Japan

[21] Appl. No.: 875,136

[22] Filed: Feb. 6, 1978

[30] Foreign Application Priority Data

Oct. 13, 1977 [JP] Japan .................................. 52/121846

[51] Int. Cl.² .............................................. A61C 3/06
[52] U.S. Cl. ......................................... 433/29; 51/270; 433/77; 433/163
[58] Field of Search ...................... 31/1, 40 R; 51/270

[56] References Cited

U.S. PATENT DOCUMENTS

| | | | |
|---|---|---|---|
| 1,374,075 | 4/1921 | Graham | 51/270 |
| 1,742,331 | 1/1930 | Voigt | 51/270 |
| 2,059,039 | 10/1936 | Sandman | 51/270 |
| 2,637,852 | 5/1953 | Globe | 51/270 |

FOREIGN PATENT DOCUMENTS 480776 7/1929 Fed. Rep. of Germany ................. 32/1

Primary Examiner—Russell R. Kinsey
Assistant Examiner—John J. Wilson
Attorney, Agent, or Firm—A. A. Orlinger

[57] ABSTRACT

An instrument for processing artificial teeth and the like, which is utilizable for collecting precious metallic powder shavings produced during the processing of the teeth, and which comprises a handy bowl-like collector and a collector plate for supplementally collecting the powders which have not been caught by the handy bowl-like collector.

9 Claims, 7 Drawing Figures

INSTRUMENT FOR PROCESSING ARTIFICIAL TEETH AND THE LIKE

This invention relates to an instrument for processing an artificial tooth, and more particularly it relates to an instrument which can collect metallic shavings produced during processing an artificial tooth made of metals and especially of precious metals.

The invention shall be explained hereinunder in greater detail with reference to the accompanying drawings.

Figure 1:
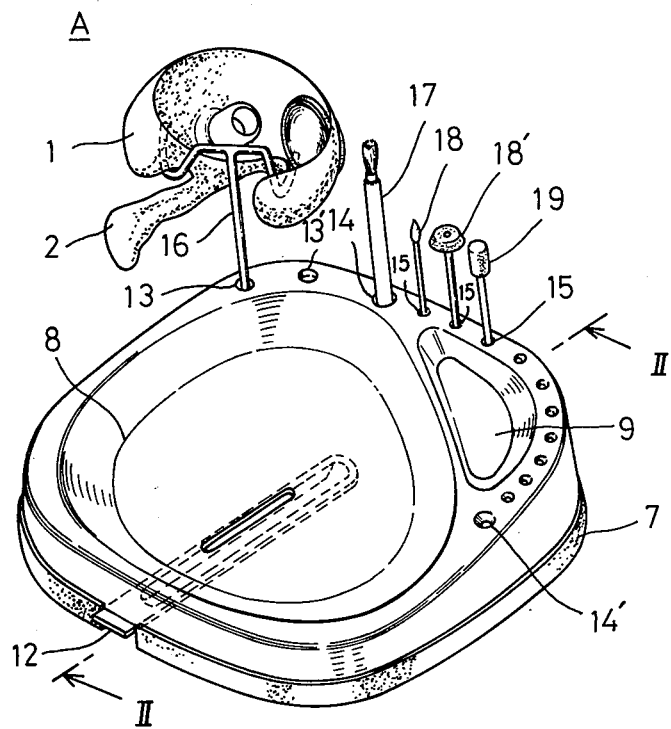
FIG. 1 is a perspective view of the instrument made in accordance with the present invention.
Figure 2:
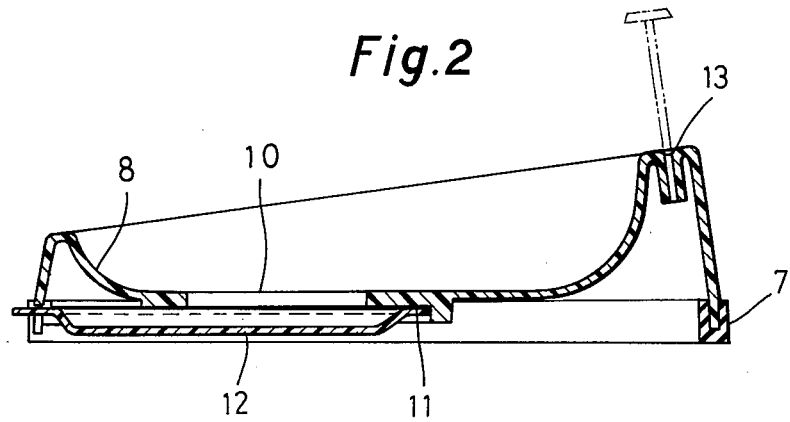
FIG. 2 is a cross-sectional view of FIG.1, taken along the line II—II.
Figure 3:
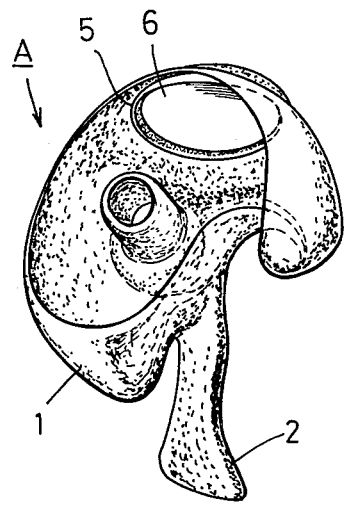
FIGS. 3 and 4 are perspective views of a mitten-like portion or collector of the instrument.
Figure 4:
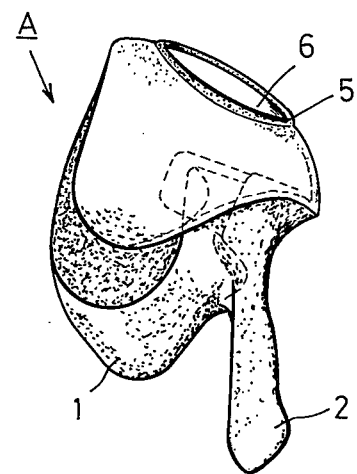
Figure 5:
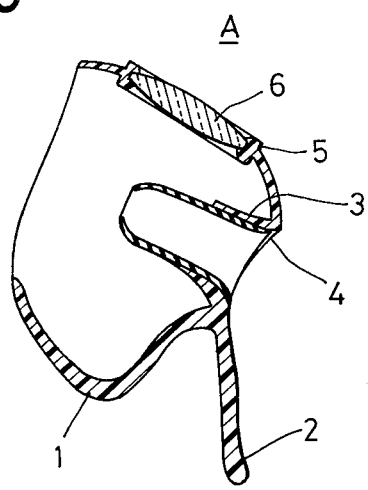
FIG. 5 is a cross-sectional view of said mitten-like handy collector.
Figure 6:
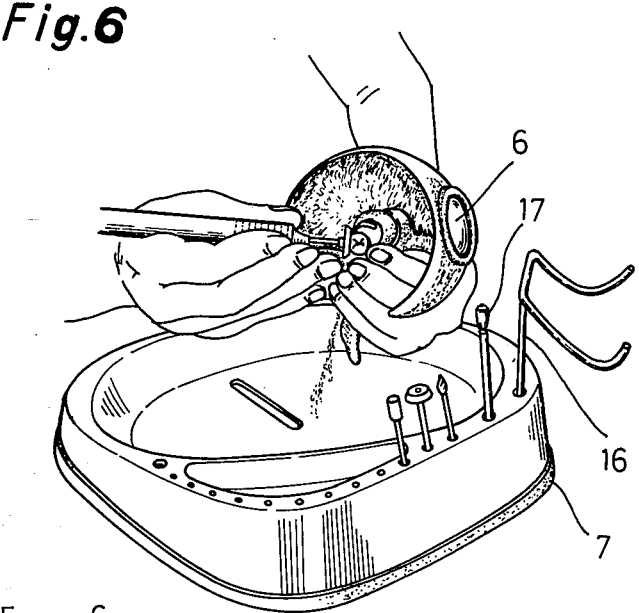
FIGS. 6 and 7 are explanatory view showing the instrument as in use.
Figure 7:
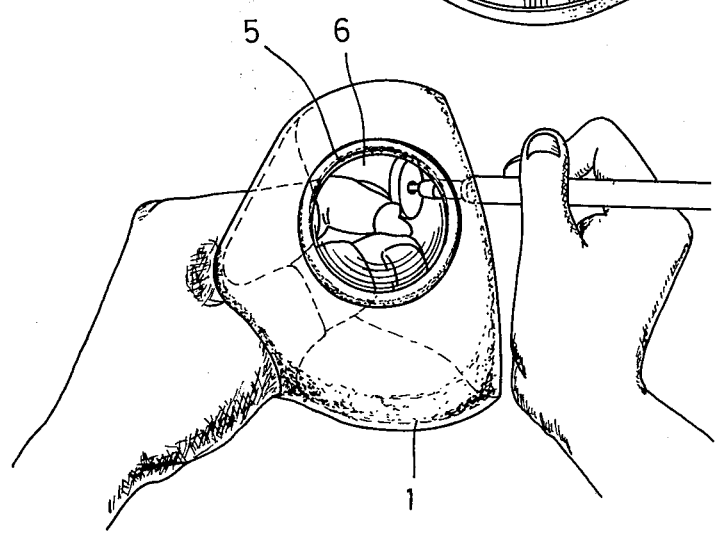

A mitten-like processor or handy collector A generally consists of a partly cut-out bowl-like body 1 which is provided with a downwardly extending grip 2. The bowl-like body 1 has also a tubular projection 3 (FIG. 5) which is provided adjacent to the bottom of the body 1 and projects inwardly of said body 1. The tubular projection 3 is insertedly fitted with an elastic tube 4 so that it can receive therein the thumb of a dental technician or dentist. A circular hole 5 is provided into the body 1 at a location opposite to the location of the grip 2, and a convex lense 6 insertedly fitted into said hole 5.

Numeral 7 indicates a collector plate having a basin 8 at its central portion and a hollow 9 at a side of the upper periphery of the basin thereof. A slot 10 is provided centrally of the basic 8. This slot is usually closed by an elongated receptacle 12 which is slidably received by a groove 11 provided in the outer surface of the bottom of the basin 8.

At a circumferential edge of the collector plate 7, there are provided a number of holes or perforations such as represented by numerals 13, 13', 14, 14', and 15. The hole 13 receives an end of a hanger 16 which in turn suspends the mitten-like processor A above the basin 8 of the plate collector. A brush 17 is removably fitted into the hole 14, for example, and grinders and the like 18, 18', 19 are insertedly and removably fitted into the holes 14 and 15.

This instrument comprising the bowl-like mitten-like processor collector A and the collector plate 7 are used, as aforementioned, for processing artificial teeth by grinding and polishing them. When the instrument is used, the thumb of a left hand is inserted into the elastic tube 4 of the processor collector A, and the artificial tooth is nipped between said thumb and the forefinger of the left hand. The grip 2 assists the mechanician to firmly hold the processor collector A on a hand. The convex lens 6 can magnify an artificial tooth under processing, whereby the processing or work of teeth can be done easily and precisely. Metallic powders, viz., silver, platinum, gold and other precious metallic powders or shavings inevitably produced by processing teeth shall be collected within the processor collector A, and a part of them shall fall onto the basin 8 of the collector plate 7.

The metallic powders collected within the bowl collector A will be brushed up by the brush 17 and then fall onto the hollow 9, while the metallic powders which fall onto the basin 8 shall be gathered by the brush 17 and fall onto the receptacle 12 through the slot 10. The powders which fall onto the receptacle 12 will be transferred into the hollow 9.

The powders gathered onto the hollow 9 shall be poured into a bottle from time to time, and be kept therein.

As explained above, the employment of the instrument made in accordance with this invention enables a dentist or dental technicians to do the processing of artificial teeth more easily, and also enables them to collect the released precious metal powders almost completely.

What is claimed is:

1. An instrument for processing artificial teeth and the like, which comprises a mitten-like collector and a collector plate, said mitten-like collector having a bowl-like configuration provided with a tubular projection for receiving the thumb therethrough, and said collector plate having a means for mounting thereabove the aforementioned mitten-like collector and having a basin for supplementally collecting thereupon powders produced in the processing the teeth.

2. An instrument as claimed in claim 1, in which the mitten-like collector also has a grip projecting outwardly from the bowl-like body portion, and has also a convex lens.

3. An instrument as claimed in claim 1, in which the collector plate has a groove provided in the outer surface of the bottom of the basin and removably closed by a receptacle, and has a hollow to one side of the basin.

4. An instrument as claimed in claim 1, in which the collector plate has a series of holes provided within and near the periphery of the upper surface of said plate for standing therein processing tools.

5. An instrument as claimed in claim 1, in which the mitten-like collector has a grip projecting outwardly from the bowl-like body portion.

6. An instrument as claimed in claim 1, in which the mitten-like collector has a lens with each of its viewing surfaces being convex and which is fixedly held in a location spaced away from the tubular projection in the body portion of the mitten-like collector so as to form a transparent part of the body portion.

7. An instrument as claimed in claim 1, in which the collector plate has a groove provided in the outer surface of the bottom of the basin and removably closed by a receptacle.

8. An instrument as claimed in claim 1, in which there is a hollow at one side of the upper periphery of the basin .

9. An instrument as claimed in claim 4, in which the collector plate has a hollow between the series of holes and one side of the basin and a groove provided in the outer surface of the bottom of the basin and removably closed by a receptacle; and the mitten-like collector has a grip extending outwardly from the bowl-like body portion and also a lens with each of its viewing surfaces being convex and which is fixedly held in a location spaced away from the tubular projection in the body portion of the mitten-like collector so as to form a transparent part of that body portion.

* * * * *

UNITED STATES PATENT AND TRADEMARK OFFICE
CERTIFICATE OF CORRECTION

PATENT NO. : 4,184,251

DATED : January 22, 1980

INVENTOR(S) : Tamotsu Kuboki

It is certified that error appears in the above-identified patent and that said Letters Patent are hereby corrected as shown below:

Column 1 line 35, "lense" should read -- lens --.

Column 1 line 38, "thereof" should be deleted.

Column 1 line 39, "basic" should read -- basin --.

Column 1 line 53, "bowl-like" should read --bowl- and--.

Column 2 claim 2 line 1, "1" should read -- 6 --.

Signed and Sealed this

Fifteenth Day of July 1980

[SEAL]

Attest:

SIDNEY A. DIAMOND

Attesting Officer

Commissioner of Patents and Trademarks